US012751863B2

(12) United States Patent
Hill et al.

(10) Patent No.: US 12,751,863 B2
(45) Date of Patent: Oct. 6, 2026

(54) SLOTTED OCULAR LENS

(71) Applicant: Ocular Instruments, Inc., Bellevue, WA (US)

(72) Inventors: Richard A. Hill, Bellevue, WA (US); Earl R. Craven, Bellevue, WA (US); Raymond D. Graham, Bellevue, WA (US)

(73) Assignee: Ocular Instruments, Inc., Bellevue, WA (US)

( * ) Notice: Subject to any disclaimer, the term of this patent is extended or adjusted under 35 U.S.C. 154(b) by 524 days.

(21) Appl. No.: 17/932,616

(22) Filed: Sep. 15, 2022

(65) Prior Publication Data

US 2023/0079304 A1 Mar. 16, 2023

Related U.S. Application Data

(60) Provisional application No. 63/245,120, filed on Sep. 16, 2021.

(51) Int. Cl.

| | |
|---|---|
| ***A61F 9/009*** | (2006.01) |
| ***A61F 9/008*** | (2006.01) |
| *A61B 17/00* | (2006.01) |

(52) U.S. Cl.

CPC .......... *A61F 9/009* (2013.01); *A61F 9/00834* (2013.01); *A61B 2017/00424* (2013.01)

(58) Field of Classification Search

CPC ......... A61B 3/12; A61B 3/1208; A61B 3/117; A61B 3/1173; A61B 3/1176; A61B 3/1216; A61B 3/0091; A61B 3/00; G02B 17/0856; G02B 17/086; G02B 5/04

See application file for complete search history.

(56) References Cited

U.S. PATENT DOCUMENTS

| | | | | |
|---|---|---|---|---|
| 2004/0041979 A1* | 3/2004 | Erickson | A61B 3/117 | 351/216 |
| 2010/0134759 A1* | 6/2010 | Silvestrini | A61B 3/117 | 351/219 |
| 2010/0265461 A1* | 10/2010 | Gille | A61B 3/117 | 351/219 |
| 2015/0313465 A1* | 11/2015 | Graham | A61B 3/117 | 351/219 |
| 2018/0310821 A1* | 11/2018 | Kalina, Jr. | A61B 17/0231 | |

* cited by examiner

*Primary Examiner* — Diane D Yabut

(74) *Attorney, Agent, or Firm* — Christensen O'Connor Johnson Kindness PLLC

(57) ABSTRACT

An occular lens, such as a laser lysis lens, is provided that is suitable for use in viewing and lysing sutures in ophthalmic procedures. The occular lens includes a lens body having an the eye contacting surface. The eye contacting surface includes a groove or slot configured to aid in localizing and fixating a ligated drainage tube of a drainage implant during ligation/suture removal.

15 Claims, 3 Drawing Sheets

SLOTTED OCULAR LENS

CROSS REFERENCE TO RELATED APPLICATIONS

This application claims the benefit of U.S. Provisional Application No. 63/245,120, filed Sep. 16, 2021, the disclosure of which is hereby incorporated by reference.

FIELD OF THE DISCLOSURE

The present disclosure provides examples of a lens suitable for use in ophthalmic procedures. In some examples, the lens is suitable for use as a laser suture lysis lens.

BACKGROUND OF THE DISCLOSURE

Replacement of one's natural lens with an interocular lens (IOL) implant is well known to address problems associated with cataracts. Cataract surgery usually involves making one or more small incision near the edge of the cornea. The surgeon uses these incisions to reach the natural lens of the eye. Using very small instruments, the surgeon removes the cataracted lens and replaces it with the IOL. In some instances, these small incisions are left to heal naturally. In other cases, a few sutures may be used to close the small incisions to aid in the healing process.

In some cases, larger incisions may be required during cataract surgery. For example, some IOL are rigid and not foldable. As a result, the larger incision allows for easier placement of the IOL. With these larger incisions, several sutures are typically required for closure. In some procedures, typically if the patient is experiencing other eye conditions, the natural (cataracted) lens is removed in one piece via a procedure called extracapsular cataract extraction. This procedure also requires a larger incision, and typically larger than that used for a procedure known as phacoemulsification, which uses ultrasound to break up the natural lens for removal. Again, with these larger incisions, several sutures are typically required for closure.

Other surgical procedures of the eye may require sutures. One such procedure is trabeculectomy. Trabeculectomy is a type of glaucoma surgery performed on the eye that creates a new pathway for fluid inside the eye to be drained. When performing trabeculectomy, a surgeon creates a flap in the conjunctiva as well as the sclera—the white part of the eye—underneath the upper eyelid. Underneath the scleral flap, a pathway is created to allow fluid to drain, which lowers eye pressure. The flap is then placed loosely back down against the sclera to protect the drainage pathway. One or more sutures may be employed to maintain the scleral flap post-surgery. The conjunctiva flap may also be retained with one or more sutures.

Some complications to these aforementioned procedures may include increased eye pressure, suture-induced astigmatism, etc. It is well known to remove one or more of the tight sutures post-surgery to address these issues or others. In other cases without these complications, the tight sutures may need to be removed several weeks after surgery.

Another trabeculectomy procedure of the eye that requires sutures involves the use of a glaucoma drainage implant. A drainage implant (also called an aqueous shunt or tube shunt) creates a new path for aqueous humor to drain from the eye. In this procedure, the surgeon makes a pocket under the conjunctiva. The plate of the implant is then placed in this pocket, supported by the sclera. The drainage implant includes a tiny drainage tube attached to the plate. The drainage tube is inserted into the anterior chamber of the eye. Aqueous fluid flows out of the eye through this drainage tube, lowering the eye pressure. The fluid collects in a pool over the plate (called a reservoir or bleb). This fluid is absorbed naturally by the body over time.

In order to remove the sutures, one procedure that surgeons may perform is laser lysis. Suture lysis by laser is usually preferred to surgical suturotomy. Serious complications such as endophthalmitis, epithelial defect, flat anterior chamber, subconjunctival hemorrhage, and hyphaema can occur after surgical suturotomy. With laser suture lysis, a lysis lens is employed to assist the surgeon in locating the sutures and for providing a complete visualization of the surgical site so that laser energy can be directed onto the sutures. The lysis lens also functions to mechanically prevent eye blinking and to apply gentle pressure against the conjunctiva in suture removal after trabeculectomy. Compression of the conjunctiva onto the scleral surface causes deturgescence and blanching of the conjunctiva allowing a clear visualization of the suture to be lysed.

In trabeculectomy or other procedures when using non-valved drainage implants, such as the Molteno-type or Baerveldt-type drainage implant, the surgeon typically occludes the drainage tube with an absorbable or meltable suture. The reason for the occlusion is to avoid early post-operative hypotony (low pressure), which can occur without the formed capsule around the drainage implant.

Postoperatively this ligature may not break or be able to be lysed in a predictable manner leaving a patient with very high intraocular pressure or it may break unattended with a patient on full glaucoma medications producing a very low intraocular pressure. This very low intraocular pressure may produce vision threatening conditions such as choroidal effusions or choroidal hemorrhage. Therefore, control over this ligature release time is imperative to post-operative patient safety.

Examples of the lens of the present disclosure aim to address lysing this ligature or other sutures.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

FIGS. 1-5 is an example of an ocular lens, such as a laser lysis lens, generally designated 20, according to an aspect of the present disclosure. The laser lysis lens 20 is suitable for use in viewing and lysing sutures in ophthalmic procedures.

As shown in FIGS. 1-4, the laser lysis lens 20 includes an elongate handle 24 to be gripped by the surgeon during use.

The handle 24 may include one or more ergonomic features. At one end of the handle 24 there is disposed a lens body 28. In an embodiment, the lens body 28 is transparent or substantially translucent. In this or other embodiments, the lens body 28 is configured to provide the surgeon with a lens magnification, for example 2× lens magnification.

Figure 1:
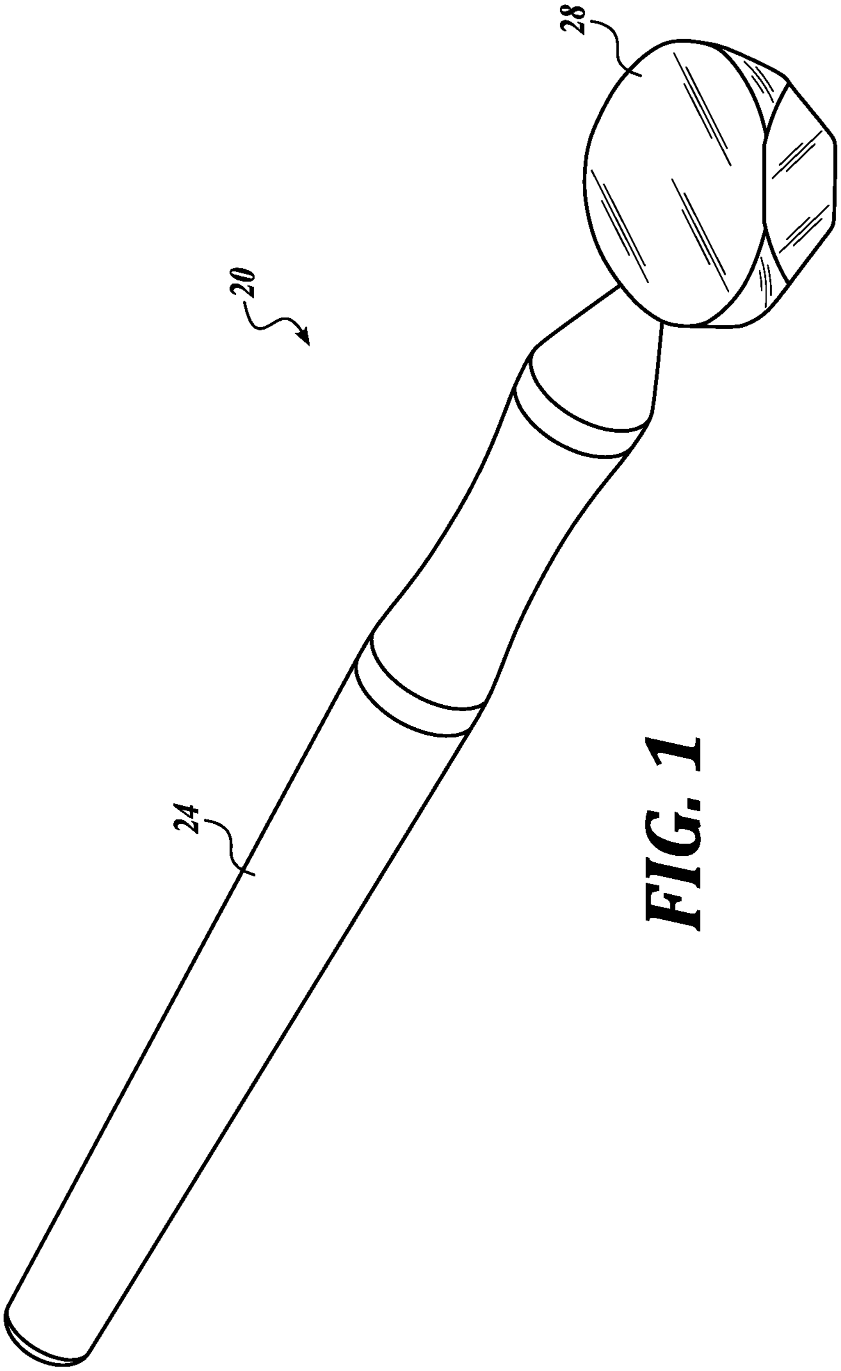
FIG. 1 is a top perspective view of one example of an ocular lens, such as a laser suture lysis lens, according to an aspect of the present disclosure.
Figure 2:
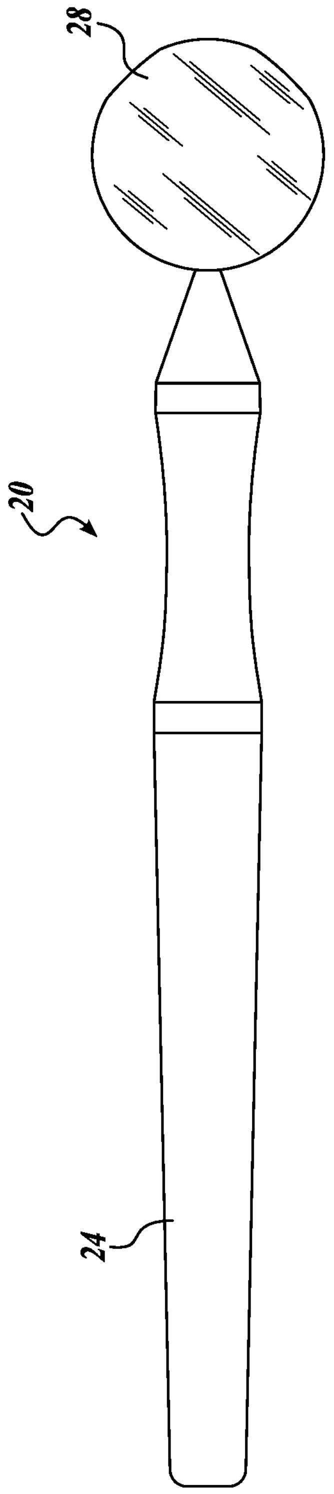
FIG. 2 is a top view of the ocular lens of FIG. 1.
Figure 3:
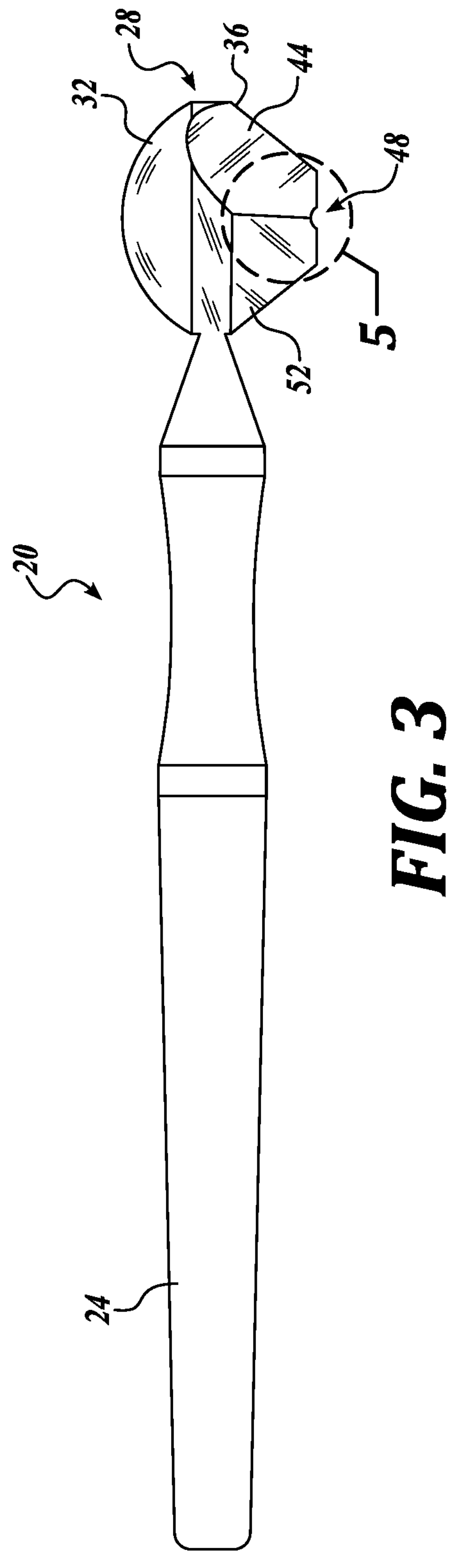
FIG. 3 is a side view of the ocular lens of FIG. 1.
Figure 4:
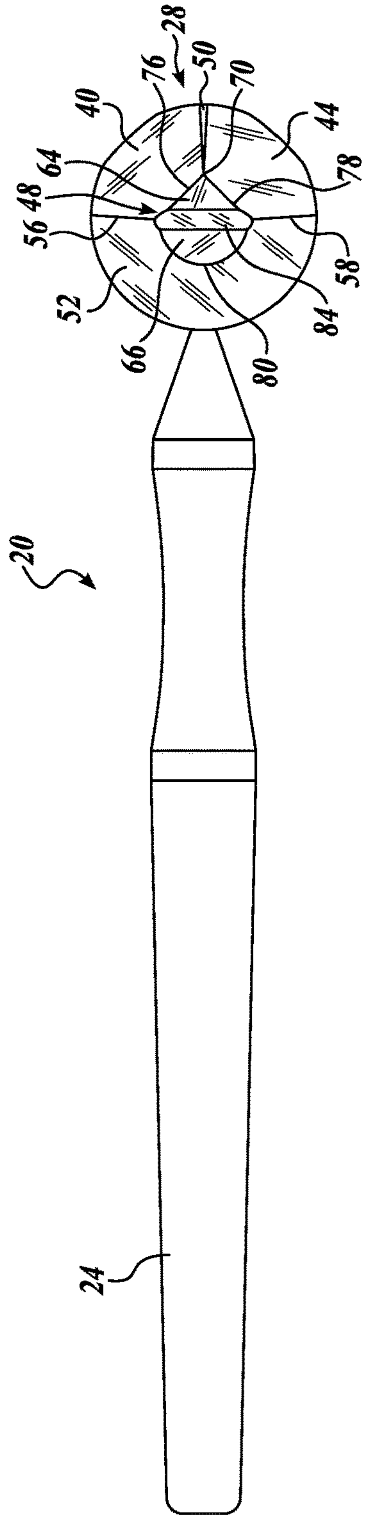
FIG. 4 is a bottom view of the ocular lens of FIG. 1.
Figure 5:
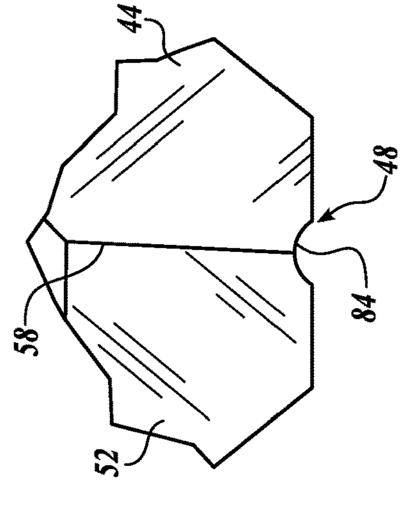
FIG. 5 is an enlarged partial view of the ocular lens of FIG. 3.

As shown in FIGS. 3-5, the lens body 28 includes a bulbous upper portion 32 and a multi-faceted lower portion 36. In the embodiment shown in FIGS. 3 and 4, the multi-faceted lower portion 36 includes a number of faces or facets, such as first and second forward facing (with respect to the handle 24) facets 40 and 44, and an eye contacting facet 48 disposed at the bottom of the lens body 28. The term "eye contacting" is used herein to mean contacting the surface of the eye, including the cornea, the conjunctiva, the sclera, etc.

The first and second facets 40 and 44 adjoin forwardly at either a centralized forward edge or at a facet of the lens body 28, opposite of the handle 24. In the embodiment shown in FIGS. 4 and 6, the forward portions of the first and second facets 40 and 44 adjoin at a centralized forward facet 50 of somewhat triangular shape. In an embodiment, the centralized forward facet 50 is aligned with the longitudinal axis of the handle 24, as shown in FIG. 4.

Figure 6:
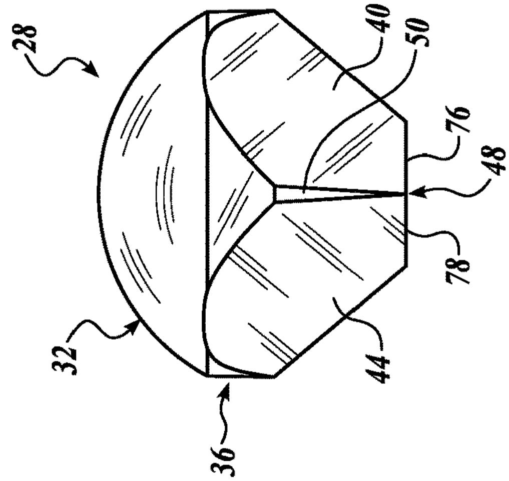
FIG. 6 is an end view of the ocular lens of FIG. 1.

The lens body 28 further includes a semi-circular wall surface 52 that extends rearwardly from the rear edges 56 and 58 of the first and second facets 40 and 44, respectively, as shown in FIGS. 3, 4, and 5. In an embodiment, the first and second facets 40 and 44 are orientated at an angle with respect to one another in order to manipulate patient eye lids, allow for smaller size or narrower fissures, etc. Each of the first and second facets 40 and 44 is also orientated at an angle with respect to the eye contacting facet 48 as shown in FIGS. 3 and 6.

In the embodiment shown in FIG. 4, the eye contacting facet 48 includes a triangular portion 64 that adjoins a semi-circular portion 66 at an interface to form a somewhat teardrop shape. In the amendment shown, the tip 70 of the triangular portion 64 is delineated by the bottom of the forward facet 50. The sides of the triangular portion 64 extending from the tip 70 are formed by the bottom edges 76 and 78 of the first and second facets 40 and 44, respectively. Similarly, the semi-circular portion 66 of the eye contacting facet 48 is delineated by the bottom arcuate edge 80 of the semi-circular wall surface 52.

In use, the teardrop shaped eye contacting facet 48 forms auxiliary lysis zones. When the lens 20 is used in laser lysis, the eye contacting facet 48 creates focal high-pressure zones that thin tissue (e.g., conjunctiva, etc.) and aid visualization. In some embodiments, the pressure applied by the lens compresses the conjunctiva against the sclera. This compression causes deturgescence and blanching of the conjunctiva, allowing a clear visualization of the suture to be lysed.

In accordance with an aspect of the present disclosure, the lens body 28 includes a polished groove or elongated slot 84 disposed in the eye contacting facet 48, as shown in FIGS. 4 and 5. In the embodiment shown in FIGS. 4 and 5, the slot 84 is orientated so as to form an interface that adjoins the semi-circular portion 66 of eye contacting facet 48 with the triangular portion 64 of the eye contacting facet 48. In an embodiment, the first and second angled facets 40 and 44 are synchronized to the position of the slot 84 so that during use the eye lids of the patient are held horizontally and the slot 84 is oriented superotemporally where 90%+ of trabeculectomy shunts are placed. With this arrangement, the lens 20 can be used with either the right hand or the left hand of the surgeon. In some embodiments, the slot 84 is positioned transverse with, and in a certain embodiment approximately orthogonal with, the longitudinal axis of the handle 24.

In some embodiments, the slot 84 is configured to facilitate fixation over, for example, a previously implanted Molteno or Baerveldt-type drainage implant. As briefly described above, drainage implant devices function by promoting simple passive diffusion of fluid out of a collection compartment. When placing the drainage implant in-situ, most of the implant device is positioned on the outside of the eye (toward the back of the eye) under the conjunctiva. A drainage device, which can be a small tube or filament, of the drainage implant, is then carefully inserted into the front chamber of the eye, just in front of the iris. Fluid from the eye drains through the drainage tube, or along the filament, into the area around the back end of the drainage implant. Collected fluid is then reabsorbed by the body.

In trabeculectomy or other procedures when using non-valved drainage implants, such as the Molteno-type or Baerveldt-type drainage implant, the surgeon typically occludes the drainage tube with an absorbable or meltable suture. The reason for the occlusion is to avoid early post-operative hypotony (low pressure), which can occur without the formed capsule around the drainage implant. Postoperatively this ligature may not break or be able to be lysed in a predictable manner, leaving a patient with very high intraocular pressure.

Figure 7:
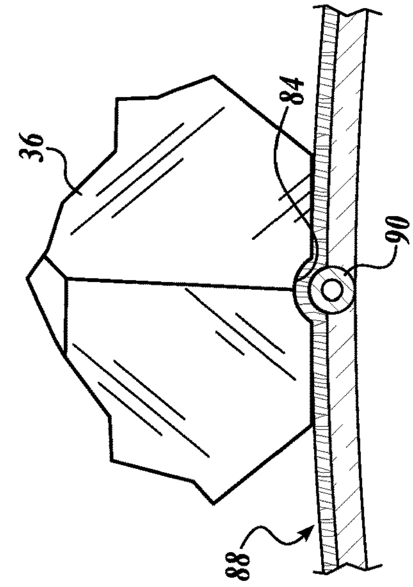
FIG. 7 is an enlarged partial view of the ocular lens of FIG. 3 fixating one example of a drainage tube of a drainage implant.

During suture removal post-operative drainage implant surgery, the lens 20, because of the configuration and positioning of the slot 84, is capable of straddling the ligated drainage tube of the drainage implant (e.g., the ligated drainage tube is at least partially received within the slot 84 when the drainage tube aligned longitudinally with the slot 84), thereby permitting a more stable placement of the lens 20 during laser suture lysis. In other words, the slot 84 allows the surgeon to localize and fixate the drainage tube, which can be poorly seen through post-operative tissue opacities. The slot 84 also thins eye tissues by direct pressure once the drainage tube is fixated to enhance laser lysis. Once fixated (e.g., between the inner surface of the slot 84 and the eye), the drainage tube extends along the elongated slot 84. At the same time, the eye contacting facet 48, or portions thereof, may contact the eye 88 as the slot 84 secures or fixates the drainage tube 90 with respect to the lens 20, as shown in the embodiment of FIG. 7.

In some embodiments, the slot 84 is rounded with a radius slightly in excess of the radius of the aqueous drainage tube of the implant to accommodate the surrounding tissue. In other embodiments, the radius is slightly less than the radius of the aqueous drainage tube of the implant. In some embodiments, the ratio of the depth of the slot 84 to the radius of the slot 84 is in the range of approximately 0.35:1.0 to approximately 0.40:1.0. In an embodiment, the slot 84 is configured to receive, or at least partially receive, the drainage tube of a Molteno-type or a Baerveldt-type drainage implant. Of course, the slot 84 of the lens 20 may be configured to fixate the drainage tube of any currently existing or future developed drainage implant or similar medical device.

In the embodiment shown, the rounded slot 84 acts as a mechanical receptor for localization and fixation of the drainage tube 90 under the post-operative tissues and allows the surgeon to cut the suture with a laser. As described briefly above, the slot 84 is oriented with respect to the angled facets 40 and 44 as well as the handle 24 to be ambidextrous and allow access to drainage implants in the superior and temporal quadrant. In other embodiments, the lens 20, for example the lower portion 36, may include four bevels or facets, the arrangement of which would then allow access to drainage implants in the superior and nasal quadrants.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Moreover, some of the method steps can be carried serially or in parallel, or in any order unless specifically expressed or understood in the context of other method steps.

In the aforementioned description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value.

Throughout this specification, terms of art may be used. These terms are to take on their ordinary meaning in the art from which they come, unless specifically defined herein or the context of their use would clearly suggest otherwise.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A laser lysis lens for viewing and lysing sutures in an ophthalmic procedure, the lens comprising:

a lens body that includes a top viewing surface and an eye contacting facet disposed at the bottom of the lens body, the eye contacting facet having a planar surface and an elongated groove extending across the planar surface, wherein the lens body is configured such that a suture to be lysed is viewed directly through the top surface of the lens body.

2. The laser lysis lens of claim 1, wherein the eye contacting facet includes a triangular portion that adjoins a semi-circular portion at an interface to form a general teardrop shape, the groove extending coincident with the interface.

3. The laser lysis lens of claim 1, further comprising first and second facets, wherein the first and second facets are disposed at an angle with respect to the eye contacting facet.

4. The laser lysis lens of claim 3, wherein the lens body includes a bulbous upper portion and a multi-faceted lower portion, the eye contacting facet disposed at a bottom of the multi-faceted lower portion.

5. The laser lysis lens of claim 3, wherein the orientation of first and second facets are synchronized to the position of the groove so that, during use, eye lids of a patient are held horizontally and the groove is oriented superotemporally.

6. The laser lysis lens of claim 3, further comprising a handle extending rearwardly from the lens body, the first and second facets facing away from the handle.

7. The laser lysis lens of claim 6, wherein the groove is oriented transversely with respect to a longitudinal axis of the handle.

8. The laser lysis lens of claim 1, wherein the groove is configured to fixate a drainage tube of a drainage implant.

9. The laser lysis lens of claim 1, wherein the groove is configured to receive, in a longitudinal manner, at least part of a drainage tube of a drainage implant.

10. The laser lysis lens of claim 1, wherein the eye contacting facet including the groove transmits light.

11. The laser lysis lens of claim 1, wherein the eye contacting facet includes first and second planar surface sections interconnected by the groove.

12. A laser lysis lens for viewing and lysing one or more sutures associated with a drainage implant, the drainage implant having a drainage tube, the lens comprising:

a lens body having bulbous upper portion and a faceted lower portion, the faceted lower portion including an eye contracting facet on a bottom of the lens body and first and second facets disposed at an angle with respect to each other and to the eye contracting facet, respectively, wherein the eye contacting facet includes a rounded, elongated slot configured to longitudinally receive at least partially the drainage tube; and a handle extending rearwardly of the lens body.

13. The laser lysis lens of claim 12, wherein the rounded, elongated slot has a depth and a radius, wherein the ratio of the depth of the slot to the radius of the slot is in the range of approximately 0.35:1.0 to approximately 0.40:1.0.

14. The laser lysis lens of claim 10, wherein the rounded, elongated slot includes a convex wall formed by the lens body, the convex wall located opposite an opening of the slot.

15. A laser lysis lens for viewing and lysing sutures in an ophthalmic procedure, the lens comprising:

a lens body that includes an eye contacting facet, the eye contacting facet having a slot, wherein the eye contacting facet includes a triangular portion that adjoins a semi-circular portion at an interface to form a general teardrop shape, the slot extending coincident with the interface.

* * * * *